United States Patent [19]
Connor et al.

[11] Patent Number: 5,075,214
[45] Date of Patent: Dec. 24, 1991

[54] METHOD OF IDENTIFYING VIRUSES

[75] Inventors: James D. Connor, La Jolla; Pramila Walpita, San Diego, both of Calif.

[73] Assignee: Regents of the University of California, Berkeley, Calif.

[21] Appl. No.: 268,761

[22] Filed: Nov. 8, 1988

[51] Int. Cl.$^5$ .............................................. C12Q 1/70
[52] U.S. Cl. ......................................... 435/5; 435/29; 435/34
[58] Field of Search ...................................... 435/5, 34

[56] References Cited

U.S. PATENT DOCUMENTS 4,521,512  6/1985  Silman ................................. 435/35

OTHER PUBLICATIONS

Kozak, M., 1986, Regulation of Protein Synthesis in Virus Infected Animal Cells, Adv. Virus Res. 31 229.
Garry, R. F. et al., 1979, Na+ and K+ Concentrations and the Regulation of Protein Synthesis in Sindbis . . . , Virology 96 108.
Dunbar, B. S., 1987, 2 Dimensional Electrophoresis and Immunological Techniques, Plenum Press, N.Y., pp. 293-294.
Doel, *Peptide Analysis of Viral Proteins, New Dev. in Practical Virology*, 143-183 (1982).
Hook et al., *Automated Microbial Identification System for Computer-Programmer Analysis of Radiolabeled Protein Banding Patterns, Developments in Industrial Microbiology*, vol. 28 (1987).
Laemmli, *Cleavage of Structural Proteins during the Assembly of the Head of Bacteriophase T4, Nature*, 227, pp. 680-685 (Aug. 15, 1970).
Walpita et al., *Abstract Form: Poster Session*, presented at 7th International Symposium on Medical Viroloby in Anaheim, Calif. on Nov. 12, 1988.
Walpita et al., 1988 ASM Annual Meeting, presented at American Society for Microbiology in Miami, Fla., during week of May 8, 1988.

*Primary Examiner*—Sam Rosen
*Attorney, Agent, or Firm*—Brown, Martin, Haller & McClain

[57] ABSTRACT

A method is described for identifying a virus infecting a host cell material, where the virus does not induce adequate or consistent host cell protein synthesis suppression, which comprises contacting a sample of the virus infected host cell material with an effective host cell protein synthesis suppression agent, allowing the virus to produce proteins characteristic of that virus in the host cell material following suppression of the host cell protein synthesis, analyzing the viral proteins so produced, obtaining from such analysis a record containing indicia uniquely characteristic of those viral proteins, and identifying the virus which produced the viral proteins by comparing the unique indicia with a library of predetermined like indicia, each of which has previously been identified with a specific virus. Preferably the host cell protein synthesis suppression agent is sodium chloride. Analysis of the viral proteins is preferably accomplished radiolabeling the proteins and separating them by electrophoresis, most preferably SDS-PAGE. The radiolabeled viral proteins can be identified by beta radiation counters or by autoradiography. The method rapidly and consistently identifies viruses to the genus, species or sub-species level, preferably by comparison to a database of like indicia using pattern recognition software.

18 Claims, 4 Drawing Sheets

| COMPARE | SAMPLE A | VIRUS 1 | DIFFERENCES |
|---|---|---|---|
| ALT MATCHES | | | |
| VIRUS 2 | | | |
| | 0.946 | | |
| VIRUS 3 | | | |
| | 0.438 | | |
| VIRUS 4 | | | |
| | 0.387 | | |
| VIRUS 5 | | | |
| | 0.286 | | |
| VIRUS 6 | | | |
| | 0.167 | | |
| VIRUS 7 | | | |
| | 0.183 | | |
| VIRUS 8 | | | |
| | 0.181 | | |
| VIRUS 9 | CHALLENGE | BEST MATCH | |
| | 0.089 | | |
| VIRUS 10 | | | |
| | 0.072 | | |

CHALLENGE : SAMPLE A     COEF. CORR. : 0.97
TYPE : INF A WSN
BEST COEF. CORR. MATCH : VIRUS 1
TYPE : INF A WSN

FIG. 3

METHOD OF IDENTIFYING VIRUSES

FIELD OF THE INVENTION

This invention relates to virology. More particularly, it relates to methods for identifying specific viruses.

BACKGROUND OF THE INVENTION

There are currently a number of different methods used to identify viruses. These generally can be classified as either of three types: "rapid diagnosis," genome identification and routine virus diagnosis.

Rapid diagnosis methods are based on antigen-antibody systems which are specific for particular viruses. These antibodies may be polyclonal or monoclonal. Typically these systems utilize visual signals such as color changes to signify a match between the antibody and the associated virus. While many of these antibody probes are available commercially, virus identification by their use suffers from a number of drawbacks. For one, the commercial probes which are available vary widely in quality, specificity and sensitivity. More importantly, however, the utility of these probes requires a significant degree of virus identification by the analyst prior to use of the probe. Because each probe is specific to one virus or a small group of related viruses, the analyst must have a good idea of which virus is involved in order to determine which type of probe is most likely to be effective. The choice of probes must be narrowed as much as possible for both practical and economic reasons. Conversely, where the general type of virus cannot be preliminarily identified, identification becomes very time-consuming and costly because of the need to work through a series of probes before the virus can be identified.

Another general category of prior art processes is genome identification. This requires specifically prepared probes of highly conserved genomic regions and use of these probes in hydridization procedures. Complete mapping requires libraries of individual probes and preparation of specially radiolabeled nucleic acid fragments. Specially equipped laboratories are the only ones who can perform such identification and the skills of specially trained analysts are necessary. Thus the technique, while effective, is costly, labor intensive and not practical for many routine identification requirements.

A third technique used is designated "routine virus diagnosis" and is based on clinical and laboratory virology. By using a number of related and sequential techniques of tissue culture and other analyses, virus identification can be accomplished. However, the techniques needed are complex and require specialized tissue cultures, analysis materials and equipment, such that the methods can be practiced by only a small number of specialized laboratories, such as those found in government agencies or universities. Further, the completion of a diagnostic report generally takes a matter of several days to many weeks, thus making the technique impractival for medical diagnosis and treatment where prompt identification of a virus is critical. Further, even many of the laboratories equipped for this type of diagnosis do not have the capability of further characterizing these isolated viruses.

There have in the past been automated techniques for identifying bacteria for electrophoresis methods, including sodium dodecyl sulfate polyacrylamide gel electrophoresis ("SDS-PAGE"). Two reports of particular interest are Hook et al. *Devel. Ind. Microbiol.*, 28, 149 (1987) [*J. Ind. Microbiol. Suppl.* 2] and Silman, U.S. Pat. No. 4,521,512. Both Hook et al. and Silman disclose a number of strains of bacteria which can be identified by obtaining an electrophoresis analysis and comparing the analysis with a library of like analyses for previously identified bacteria. The techniques described work quite well for bacterial analysis, since bacterial protein analysis is unaffected by the presence of host cell proteins. In addition, bacteria are relatively complex organisms and are able to grow in synthetic media outside the cell. Upon routine electrophoretic separation, they produce many protein bands which are microbe specific and thus can be readily identified using simple pattern recognition software. Viruses, on the other hand, require live cell systems for growth. When viral cultures are subjected to SDS-PAGE, very few viral protein bands are seen among hundreds of bands for cell specific proteins.

The Silman patent suggests that its disclosed method could be applicable to the identification of "viruses or other microorganisms which require a host cell for metabolic activity." However, it can be shown that the Silman technique is applicable only to those few viruses which spontaneously and consistently suppress the synthesis of proteins of host cells in which they replicate. The viruses of consequence among these few are the herpes simplex viruses, HSV-1 and HSV-2, which are also the only viruses mentioned by Silman. Consequently, with this exception, the Silman method is applicable only to microbes which grow in synthetic media. For most viruses, the continued production of proteins by the host cell effectively precludes any consistent and accurate virus identification by known electrophoretic techniques.

It would therefore be of great value to have a virus identification technique which could be performed relatively rapidly using well-known readily available analysis methods and which would be capable of being performed on a routine basis by a wide number of analytical laboratories or even by individual researchers. Further, it would be advantageous to have a technique which would permit the immediate screening and identification of a wide variety of related and unrelated viruses with a single procedure, so that an analyst could identify a virus even with little or no preidentification of the virus. It would also be advantageous to have an identification procedure which could be used in a conventional virology laboratory.

SUMMARY OF THE INVENTION

The invention herein is a method of identifying a virus infecting a host cell material, where the virus does not induce adequate or consistent host cell protein synthesis suppression, which comprises contacting a sample of the virus infected host cell material with a host cell protein synthesis suppression agent, allowing the virus to produce proteins characteristic of that virus in the host cell material following suppression of the host cell protein synthesis, analyzing the viral proteins so produced, obtaining from such analysis a record containing indicia uniquely characteristic of those viral proteins, and identifying the virus which produced the viral proteins by comparing the unique indicia with a library of predetermined like indicia, each of which has previously been identified with a specific virus.

In preferred embodiments, the host cell protein synthesis suppression agent is sodium chloride.

For the purposes of this invention, the term "viral proteins" means not only the proteins themselves but also protein digests produced from the viral proteins. The invention herein can be performed on either material. Also, "adequate" suppression of host cell proteins means suppression to the degree that the concentration of host cell proteins in the medium is sufficiently low so that they do not have a significant effect on the detection and quantifying of the viral proteins. An occasional host cell protein band which is not suppressed may appear in the analysis record but such are readily identified as being of cell origin and do not affect the present viral protein identification process. In many cases suppression of the host cell protein synthesis will be virtually complete.

Analysis of the viral proteins can be accomplished by known techniques, including chromatography, isoelectric focusing and the preferred analysis method, electrophoresis, most preferably SDS-PAGE. Fore some techniques the viral proteins will be tagged prior to separation by any conventional labeling technique, such as radiolabeling or chemiluminescence. In other cases the proteins can be tagged after separation, as by staining. The viral proteins will be identified by conventional methods appropriate to the type of labeling used, such as beta radiation counting or autoradiography for radiolabeled proteins. It will of course be evident that different analytical techniques will produce different types of indicia and that viral identification must be made using a library of indicia previously obtained using the same technique.

Preferably the identification will be made with the aid of pattern recognition software.

BRIEF DESCRIPTION OF THE DRAWINGS

FIG. 3 is an illustration of a computer monitor display occurring during a computer-aided virus identification database search showing a typical match between the subject virus (in this case Influenza A WSN) and the database correlation identifying the virus correctly. Also shown are the nine next-best alternative matches offered by the software.

DETAILED DESCRIPTION AND PREFERRED EMBODIMENTS

Figure 1:
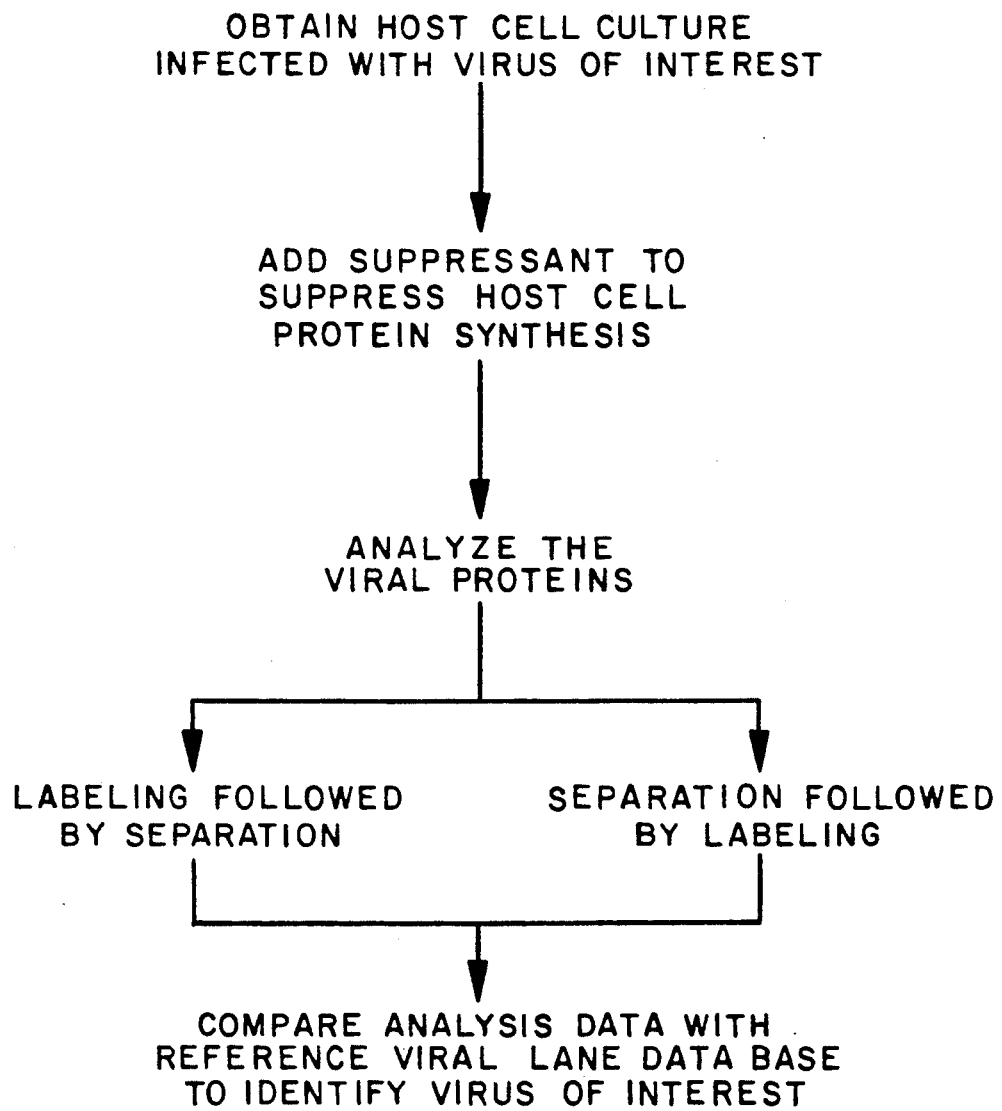
FIG. 1 is a schematic flow diagram showing the basic steps in the method for identifying a virus.
Figure 2:
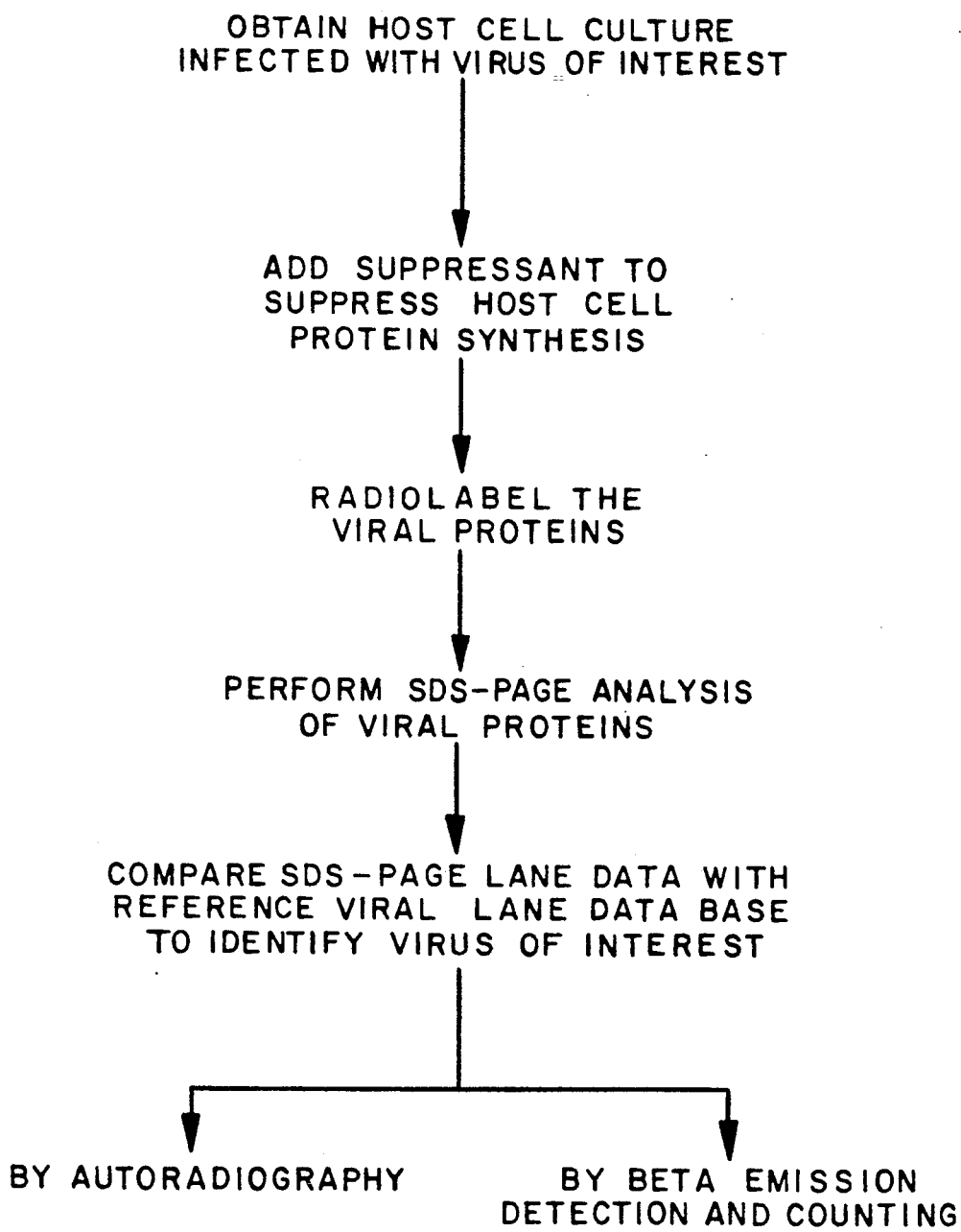
FIG. 2 is a schematic flow diagram showing the steps in the method for identifying a virus by radio labeling, SDS-PAGE and autoradiography or beta emission detection.

The technique of this invention relies upon the recognition that each species (or even sub-species) of virus infecting a host cell causes production of a set of viral proteins unique to that particular virus in the host cell. One might think that it would be a simple matter to identify those proteins by conventional protein identification techniques and then in turn identify the originating virus. In practice, however, this has turned out not to be possible except for a very limited number of viruses. Various types of viral protein identification based on prior art techniques previously known in bacteriology have proved to be inconsistent in results. Clearly, of course, a technique which does not consistently identify the viruses accurately is of no use.

The present invention involves the recognition that the normal synthesis of proteins by the host cell masks and distorts the analysis of the viral proteins and prevents the consistent and unequivocal identification of the latter. More particularly, therefore, the invention herein involves the discovery that a certain limited number of suppressant compounds can be used at a critical point in the analysis procedure to adequately and consistently suppress host cell protein synthesis without also suppressing the viral protein production, thus allowing the viral protein synthesis to proceed and produce a protein inventory that is unique to the virus in question and which can be readily identified in the absence of any significant amount of host cell protein.

As with any identification procedure, the utility of the present invention involves the previous compilation of a database or library of the unique analysis results or "fingerprints" of identified viruses. This database is created by using the same analysis technique used for determining the identification of an unknown virus. Most commonly the library or database can be in the form of lane data from autoradiographs or beta emission data for electrophoretic migration bands. The data obtained from the analyses (such as SDS-PAGE) relate the variation of molecular weight of each radiolabeled protein with electrophoretic migration distance. Typical graphs of such data are those shown in FIGS. 3 and 4. Each set of data is unique to the viral proteins generated by the particular virus in question. The data, either as initially obtained (as with an emission detector) or from autoradiographs or resultant graphs, can also be digitized and entered into a computerized database where they can be rapidly scanned for matches by pattern recognition software. The size and structure of the database will be important in the ease of use of the present identification process. The larger the database, of course, the more viruses can be identified. On the other hand, a large database requires a proportionally long time to search. Therefore, it is desirable to have the database constructed such that it can be subdivided into groups of related viruses so that, when the analyst can make some preliminary limiting determinations about the nature of the suspect virus (as is usually the case), the amount of search required can be significantly lessened.

The method of this invention is practiced by first obtaining a sample of the host cell material. Since the host cell's own protein synthesis will subsequently be suppressed, the nature of the particular host cell is not critical, except to the extent that it must be a cell line in which the suspect or desired virus will rapidly and effectively produce viral proteins. Cell lines used have been HEp-2, foreskin fibroblasts and LLC-MK2.

For the creation of the library or database, the host cell line is infected with a known virus. In the case of identification of an unknown virus, the sample host cell material when obtained is the infected sample.

The infected sample is then cultured in a growth medium until a cytopathogenic effect (CPE) of 3+ is observed. The growth medium of the culture is then replaced with a maintenance medium and incubated at human body temperature for a short period, following which the host cell protein synthesis suppression agent is added. The growth medium must be free of any material which might interfere with later steps in the analysis method. For instance, if it is desired to radiolabel the proteins with radio-methionine, the maintenance medium must be methionine-free.

The suppressant or suppression agent must be one which, within its operable concentration range, consistently and adequately suppresses the host cell protein synthesis but which does not simultaneously suppress production of the viral proteins. Its use is critical to the identification of most viruses by this method, since most viruses do not induce adequate and consistent virus-induced host cell protein synthesis suppression, and many do not cause suppression at all. Thus this method, including the suppressing agent, may be used advantageously with not only the large number of viruses which do not induce suppression at all, but also with those viruses which do provide an insufficient degree of virus-induced host cell protein synthesis suppression. The preferred suppressant is sodium chloride. A number of other possible suppressants were examined, including actinomycin D, but none were found to produce consistent and complete host cell protein synthesis suppression. It will be evident, however, that there are other potential suppressants which have not been specifically examined, and it is therefore intended that this invention include all suppressants which have suppressant properties substantially equivalent to or better than sodium chloride.

The minimum suppressant concentration will be determined as the minimum necessary for effective suppression of host cell protein synthesis. This in turn will of course be dependent on the particular host cell and the virus, and the amount can be readily determined by running parallel experiments using spectrum of concentrations of the suppressants. As an example, a series of tests using NaCl as the suppressant was run with respiratory syncytial (RS) virus (subgroup A) infecting HEp-2 cells and compared to a similar series run on uninfected HEp-2 cells. The concentrations of NaCl ranged from 0.05M to 0.2M. For both the infected and uninfected HEp-2 host cell samples, host cell protein suppression was significant at 0.13M and found to be essentially fully complete at 0.15M. The viral protein production was not significantly affected by the NaCl concentrations up to 0.2M., The maximum suppressant concentration is determined as the amount where a suppressing effect on the viral protein synthesis will begin to be observed. Consequently, it is preferred that the operating concentration be maintained at a level at or slightly above the minimum concentration at which the host cell protein synthesis is fully suppressed. In the example just mentioned, subsequent tests using the HEp-2 cells were run with 0.15M NaCl and consistently good identification for a number of viruses were obtained.

The addition of the suppressant to the infected cell culture is started shortly prior to separation as a precaution against reversibility of the host cell protein synthesis suppression. If the proteins are to be labeling prior to separation, the addition of the suppressant will continue throughout the labeling step.

Labeling (or "tagging") of the proteins can be done by any conventional technique, including chemiluminescence, staining or radiolabeling. Preferred is to radio-label the proteins prior to separation using a conventional radioisotope. As an example, where one uses a methionine-free medium as mentioned above, the labeling agent can be $^{35}$S-methionine. The extent of radiolabeling needed will be that commonly used for labeling proteins. For instance, one hour incorporation of $^{35}$S-methionine was found to be satisfactory for all viruses except RS virus, for which four hour incorporation of the $^{35}$S-methionine was preferred. Normally addition of 50 microcuries per milliliter of the $^{35}$S-methionine was found to be adequate for identification purposes. Once the desired amount of labeling agent is incorporated, the labeling procedure can be terminated in a conventional manner and the samples subjected to the normal preparation for the protein identification technique to be use with the pre-determined viral database.

The cultured samples, which may be labeled, are then subjected to the desired protein separation method, such as chromatography, electrophoresis or isoelectric focusing. The preferred method is the well-known SDS-PAGE technique, as described in the above mentioned Hook et al. and Silman references. In this technique labeled proteins are separated by electrophoresis and the proteins spread out, concentrating at various points along a band on a plate or paper medium as determined by the degree of mobility of each of the proteins in the electrophoretic environment. The location and concentration of each of the labeled proteins can then be made visible by application of a photosensitive film to the plate or paper. The radiolabeled proteins expose the film, which can subsequently be developed to provide a visual record (an "autoradiograph") of the patterns of the band. If the sample is to be analyzed by staining after SDS-PAGE, the unlabeled proteins are stained after having been spread out by the SDS-PAGE procedure and the staining patterns observed.

Figure 4:
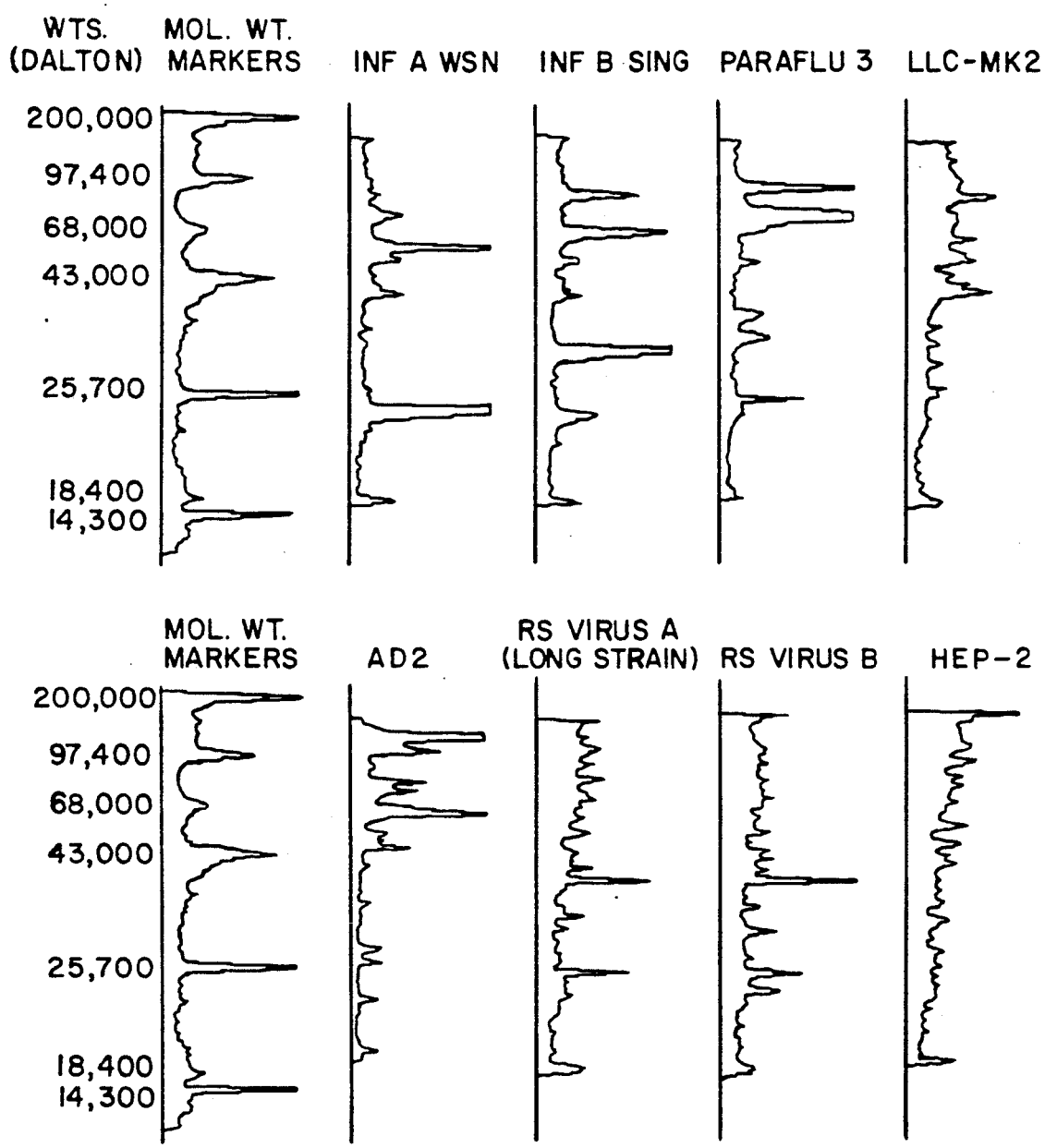
FIG. 4 illustrates typical radiolabeled viral protein profiles as produced by SDS-PAGE and measured with a beta emission detector for virus infected cell lysates.

In either case, as noted above, the pattern data can be digitized for computer analysis, or the autoradiograph or stain record of the unknown sample can be visually compared with library records of the proteins of known viruses. Alternatively, the band patterns can be scanned by an appropriate recognition device, such as a spectrophotometer or a radiation sensitive instrument (e.g., a beta emission counter for $^{35}$S-labeled proteins) and the amount of the specific indicium (e.g., stain or radiation) present at each point along the band can be directly digitized and, if desired, plotted as illustrated in FIGS. 3 and 4. If the sample is of a host cell infected with a known virus, the pattern data obtained can be directly entered into the relevant data base. If the sample is infected with an unknown virus, the data can be compared by pattern recognition software with the equivalent data in the database to determine which previously predetermined pattern is most closely matched by the data of the sample in question and thus to provide the identification of the unknown virus. The data base can be expanded by data acquisition experiments involving deliberate infecting of uninfected host cells with known viruses. In addition, the database can also be expanded by entering the pattern data for previously uncataloged viruses obtained from analyses in which the virus is identified by the prior art techniques.

To test the efficacy of this technique, a 32-member data base was constructed to include 26 viral profiles of reference viruses, as shown in the Table below.

| DATABASE OF ROUTINELY ISOLATED VIRUSES | | | |
| --- | --- | --- | --- |
| Adenovirus | 12* | Parainfluenza | 3 |
| Influenza A | 2 | Influenza B | 6 |

| DATABASE OF ROUTINELY ISOLATED VIRUSES | | | |
|---|---|---|---|
| RS Virus** | 3 | Cell Controls | 6 |

*Duplicate protein profiles of adenovirus serotypes 2, 4, 7a, 9, 12 and 19.
**Subgroups A and B To ensure consistent matching, most profiles included were present in duplicate and were generated in separate gels and in separate experiments. The database also included six profiles of uninfected cell lines of the types usually routinely used to culture the reference viruses. The subsequent database search for pattern recognition was done in two stages using two numerical protocols. Initial search involved automatic comparison of the unknown protein profile with the reference profiles in the database using the Fast Fourier Transform algorithm. The reference protein profiles in the database were stored as transform data for computational efficiency, economy of memory and rapid data storing. Thereafter, as a second step, the ten best matches obtained by this method were pattern matched with the unknown protein profile using Pearson's Correlation Coefficient r, a quantitative means of determining protein profile similarities. With the particular software used, the result of the final search was displayed on a video terminal monitor as the "best correlation match" as shown in FIG. 3. This software also provided a numerical ranking of the nine next best matches, based on their r value (which were also shown on the monitor for the user's information). The accuracy of the matching was confirmed by further correlation of multiple profiles of the same virus.

Depending on the particular software used, confidence in the virus identifications can be readily obtained at the genus, species or subspecies level. While this degree of confidence has previously been obtained in bacteria identification, it has not heretofore been possible to obtain virus identification at these taxonomic levels, because viral proteins generate far fewer bands than do bacterial proteins, making pattern recognition essentially impossible in the presence of unsuppressed host cell proteins.

The particular pattern recognition software used will not be critical, as long as the software can sufficiently distinguish the viral protein bands to the taxonomic level desired. Thus various algorithms and statistical methods can be used if adequate resolution is obtained. The software described above was found to be satisfactory to the genus level. Those skilled in the art will have no difficulty identifying software capable of identifying viruses to the species or, frequently, the sub-species level.

In further experiments, 113 viral protein profiles and 12 uninfected cell controls were challenged against the aforementioned database for virus identification. In each case the match of the first choice from the database was correct to the genus level.

It will be evident that there are aspects of the invention which are not specifically described above but which are clearly within the scope and spirit of the invention. The above description is therefore intended to be exemplary only, and the full scope of the invention is to be limited solely by the appended claims.

We claim:

1. A method of identifying a virus infecting a host cell material, where said virus does not adequately and consistently induce suppression of host cell protein synthesis, which comprises:

a. contacting a sample of said virus infected host cell material with a suppression agent which adequately and consistently suppresses host cell protein synthesis;
b. allowing said virus to produce proteins characteristic of that virus in said host cell material following suppression of said host cell protein synthesis;
c. analyzing the viral proteins so produced;
d. obtaining from such analysis a record containing indicia uniquely characteristic of those viral proteins; and
e. identifying said virus which produced said viral proteins by comparison of said unique indicia with a library of pre-determined like indicia, each of which has previously been identified with a specific virus.

2. A method as in claim 1 wherein said suppression agent is sodium chloride or a compound possessing the property of host cell protein suppression for respiratory syncytial virus (subgroup A) infecting HEp-2 cells at least equal to that of a 0.13–0.2M sodium chloride solution.

3. A method as in claim 2 wherein said suppression agent is sodium chloride.

4. A method as in claim 3 wherein said sodium chloride is present in a concentration of at least 0.15M.

5. A method as in claim 4 wherein said sodium chloride is present in a concentration in the range of from about 0.15M to about 0.2M.

6. A method as in claim 1 wherein said analysis of said viral proteins comprises separating and labeling said proteins.

7. A method as in claim 6 wherein said separation is by electrophoresis, chromatography or isoelectric focusing.

8. A method as in claim 7 wherein said separation is by electrophoresis.

9. A method as in claim 8 wherein said separation is by sodium dodecyl sulfate polyacrylamide gel electrophoresis.

10. A method as in claim 6 wherein said labeling precedes said separation.

11. A method as in claim 10 wherein said separation is by electrophoresis and is preceded by radiolabeling of said proteins.

12. A method as in claim 11 wherein said electrophoresis is followed by detection of radioemission data proportional to protein molecular weight and migration.

13. A method as in claim 12 wherein said data are converted to digital form.

14. A method as in claim 6 wherein said labeling follows said separation.

15. A method as in claim 14 wherein said separation is by electrophoresis and is followed by staining of said proteins.

16. A method as in claim 1 wherein said viral proteins are radiolabeled and said indicia comprise radioemission data from said radiolabeled proteins.

17. A method as in claim 1 wherein said viral proteins are stained and said indicia comprise stain pattern data from said stained proteins.

18. A method as in claim 1 wherein said comparison comprises using pattern recognition computer software to match said unique indicia with like indicia in a database and identification of the specific indicia in said database which most closely resembles said unique indicia.

* * * * *